United States Patent [19]

Jurim

[11] Patent Number: 4,632,660
[45] Date of Patent: Dec. 30, 1986

[54] PROSTHETIC DENTISTRY

[76] Inventor: Adrain S. Jurim, 3 Wood Rd., Great Neck, N.Y. 11024

[21] Appl. No.: 488,884

[22] Filed: Apr. 26, 1983

[51] Int. Cl.⁴ .................................................. A61C 5/00
[52] U.S. Cl. .................................... 433/215; 433/204
[58] Field of Search ................... 433/212, 222, 9, 202, 433/204

[56] References Cited

U.S. PATENT DOCUMENTS

| | | | |
|---|---|---|---|
| 356,833 | 12/1886 | Grout | 433/222 |
| 1,712,043 | 5/1929 | Limbarth . | |
| 2,078,707 | 1/1982 | Griffith . | |
| 2,910,351 | 10/1959 | Szpak et al. | 427/96 |
| 3,004,343 | 10/1961 | Rydin . | |
| 3,046,657 | 7/1962 | Menter . | |
| 3,327,016 | 6/1967 | Lee . | |
| 3,375,582 | 4/1968 | Myerson . | |
| 3,422,535 | 10/1965 | Johnson . | |
| 3,423,829 | 1/1969 | Halpern . | |
| 3,423,830 | 1/1969 | Halpern . | |
| 3,468,028 | 9/1969 | Sunter . | |
| 3,483,618 | 12/1969 | Andrew . | |
| 3,647,498 | 3/1972 | Dougherty . | |
| 3,760,502 | 9/1973 | Hirsch . | |
| 3,847,688 | 11/1974 | Gillice | 156/2 |
| 3,899,437 | 8/1975 | Regan | 252/106 |
| 3,936,939 | 2/1976 | Faunce . | |
| 3,986,261 | 10/1976 | Faunce . | |
| 4,117,595 | 10/1978 | Ibsen | 433/218 |
| 4,129,946 | 12/1978 | Kennedy . | |
| 4,194,907 | 3/1980 | Tsai . | |
| 4,210,447 | 7/1980 | Tsai . | |
| 4,256,603 | 3/1981 | Ibsen . | |
| 4,292,236 | 9/1981 | Ibsen . | |
| 4,294,349 | 10/1981 | Ibsen . | |
| 4,376,673 | 3/1983 | Cheung | 433/216 |
| 4,380,432 | 4/1983 | Orlouski et al. | 433/219 |
| 4,433,959 | 2/1984 | Faunce . | |
| 4,473,353 | 9/1984 | Gregg | 433/215 |
| 4,475,892 | 10/1984 | Faunce . | |

FOREIGN PATENT DOCUMENTS 2078707 1/1982 United Kingdom .

OTHER PUBLICATIONS

Jochen, et al, "Composite Resin Repair of Porcelain Denture Teeth", J. Prosthet. Dent., vol. 38, No. 6, 12/77—p. 674.
Highton et al, "Effectiveness of Porcelain Repair Systems," J. Prosthet. Den, vol. 42, No. 3, 9/79—pp. 292-294.
Horn, "A New Lamination: Porcelain Bonded to Enamel," N.Y.S. Dental J., Jun./Jul. 1983, pp. 401-403.
"Advanced Student's Handbook-Dental Technology," vol. 1, Kerpel School of Dental Technology, copyright 1965.
"The Progress & Development of All Ceramic Phases of Dental Technology" Kerpel, copyright 1965.
Slocum, "The Technic of Porcelain Jacket Crowns" 10/27/24—The Dental Digest.
Rentz & Wickwire "Enamel Pretreatment: A Critical Variable in direct Bonding Sys. Am. J. Orthod., Nov. 1973.
Bowen, "Adhesive Bonding of various materials to hard tooth tissues, VI JADA, vol. 74, pp. 439-445, Feb. 1967.
Rasmussen, "Fracture Studies of Adhesion" J. Dent Res., vol. 57, No. 1. pp. 11-20, Jan., 1978.
Clinical Research Associates Newsletter, vol. 2, Issue 10, Oct. 1978.
Barkley, Faunce and Gaw, "Esthetic Tooth Restoration" Dental Survey Jan. 1979.
Rapis, Fan and Powers, "Properties of micorfilled and visible light-cured composite resins" JADA, vol. 99, Oct. 1979.
Hunt and Rafetto, "Full Circle in Ceramics—The Dev. of a New Porcelain Fused to Metal Restoration" vol. 1, No. 1, Compendium on Continuing Ed., Feb., 1980.
Barkely, Faunce & Fleming, "Report on a Case of Maxillary & Mandibular Lamn Veneers" J. Indiana Dent. Assn., vol. 59, No. 5, Sep./Oct. 1980.
Clinical Research Assoc. Newsletter, vol. 4, Issue 11, Nov. 1980.
Cammarato & Heyde, "A Restoration Sys. for the Repair of Defects in Anterior Teeth" Dental Clinics of North America, vol. 25, No. 2, Apr. 1981.
Boyer & Chalkey, "Bonding Between Acrylic Laminates & Composite Resin" J. Dent. Res., vol. 61, No. 3, pp. 489-492, Mar. 1982.
Johnson, "Use of Laminate Veneers in Pediatric Dentistry: Present Status and Future Developments," Pediatric Dentistry, vol. 14, No. 1, Mar. 1982.
Goteiner & Sonnenberg, "Maintenance of Laminate Veneers, " Clinical Preventive Dentistry, vol. 4, No. 1, Jan.-Feb. 1982.
Literature re Mastique laminates by Caulk.
Literature re Myerson's laminates by Myerson Tooth Corp.
Literature re Rembrant Shade Kit by Den-Mat.

Primary Examiner—Robert Peshock
Attorney, Agent, or Firm—Morgan & Finnegan

[57] ABSTRACT

Am inprovment in prosthetic dentistry which allows a porcelain veneer facing to be permanently affixed directly to a natural or virgin tooth without significant grinding or reduction of the tooth surface. The improvement consists in a method, and the product produced thereby, of chemically etching a selected portion of a porcelain veneer facing, which is thereafter directly affixed to an acid-etched natural or virgin tooth surface by a suitable bonding composition. A selected portion of the porcelain veneer is covered by a layer of a waxy protective material and the facing is thereafter contacted with a hydrofluoric acid solution of controlled concentration under controlled time and temperature conditions so as to partially dissolve or etch the unprotected portion of the facing. The porcelain veneer facing is thereafter capable of being bonded directly to an acid-etched natural or virgin tooth with great strength and durability.

12 Claims, No Drawings

PROSTHETIC DENTISTRY

BACKGROUND AND OBJECTS OF THE INVENTION

1. Field of the Invention.

The present invention relates to an improvement in prosthetic dentistry. More particularly, the invention relates to the art of forming an acid-etched surface on a porcelain veneer facing using an aqueous acidic solution and subsequently forming a product comprising a porcelain veneer facing bonded directly to a natural or virgin tooth without requiring the conventional grinding and capping procedures and without requiring significant reduction of the tooth surface.

2. Description of the Prior Art.

At the present time, probably the most common technique for covering a discolored or disfigured tooth is to grind the tooth down to a stub or post and then affix a tooth "cap" onto the post, the cap often consisting of porcelain bonded to gold. This technique, however, is undesirable, particularly in the case of children, because it requires that the natural or virgin tooth largely be removed in its preparation for receipt of the cap.

In attempt to overcome the disadvantages of grinding, certain plastic shells have been used to cover discolored or disfigured teeth. The most common commercially used plastic materials for modifying an individual's tooth arrangement or disfigurement have been various types of thermoplastic resins. These materials usually come as ready-to-use plastic shells which slip over the patient's tooth and are attached thereto by a suitable adhesive after acid-etching the virgin or natural tooth surface. Alternatively, the plastic resin material has been applied as a loose composite medium which is grossly applied to the tooth surface and thereafter ground, shaped and polished in the oral chamber. These plastic materials, however, suffer from many other disadvantages, such as their tendency to absorb water, discolor, wear down and cause gum tissue irritation. Consequently for example, the use of plastic shells or veneer facings has been primarily restricted to the relatively short term requirements of covering discolorations in the "baby" teeth of small children.

Porcelain has long been considered the ideal material for preparing prosthetic dental devices since it is the material which most closely resembles natural or virgin teeth. However, because of the extreme surface imperviousness of porcelain, it has heretofore been unknown, and thought to be impossible, to securely fix a porcelain veneer facing to a natural or virgin tooth. In particular, it has heretofore been found that the conventional methods of acid-etching or grinding down of the natural tooth were unsatisfactory because the porcelain veneer facing tended to slip off and become dislodged when subjected to a normal amount of masticatory stress.

Prior to the instant invention, it was not known how to etch porcelain. Although it has been previously known to acid-etch metal, that has been done through an electronic process, which cannot be used with porcelain, a highly insulative material. Heretofore, it was thought porcelain could not be chemically etched and that it would be necessary to in some, as yet unknown, way adapt the acid-etching process for use with porcelain.

The present invention overcomes the deficiencies of the prior practices by the discovery of a method for chemically etching the surface of a porcelain veneer facing which is to be affixed to a tooth, whereby the porcelain facing may be bonded directly to an acid-etched natural or virgin tooth surface by conventional bonding techniques, resulting in a porcelain veneer on a natural tooth with a much stronger and longer lasting bond than was heretofore known or thought possible.

3. Objects of the Invention.

It is therefore a principal object of the present invention to provide a porcelain veneer facing which may be securely affixed to a natural or virgin tooth without significant grinding or reduction of the tooth surface.

Another object of the present invention is to provide a method for acid-etching a selected portion of a porcelain veneer facing.

Another object of the present invention is to provide a method for dental prosthesis comprising a porcelain veneer facing securely affixed directly to a natural or virgin tooth surface by a bonding composition.

Another object of the present invention is to eliminate the shortcomings of the previously conventional techniques for "capping" a discolored or disfigured natural or virgin tooth.

Objects and advantages of the invention are set forth in part herein and in part will be obvious herefrom, or may be learned by practice with the invention, the same being realized and attained by means of the instrumentalities and combinations pointed out in the appended claims.

The invention consists in the novel products, arrangements, combinations, steps, processes and improvements herein shown and described.

DESCRIPTION OF THE PREFERRED EMBODIMENT

In accordance with the present invention it has been surprisingly discovered that a porcelain veneer facing surface can be chemically etched by contacting the porcelain veneer facing with an aqueous acidic solution of predetermined concentration at a predetermined temperature for a predetermined period of time.

As preferably embodied, and the only known acid to date which will chemically etch porcelain, the aqueous acidic solution of the invention is hydrofluoric acid. Hydrofluoric acid has been found to produce highly satisfactory results and is therefore set forth as the preferred mode of carrying out the invention. It has been found that certain other well known acids have little or no effect on porcelain, including nitric acid, hydrochloric acid and phosphoric acid. Nevertheless, it is believed that other acid solutions may be found to etch porcelain with satisfactory results and it will be understood that such solutions are within the scope of the present invention.

As here preferably embodied, the operating conditions for the use of the aqueous hydrofluoric acid solution include the use of a solution which has an acid concentration in the range of between about 10–15% for approximately 12 to 15 minutes at room temperature.

The rate of attack of the acid-etching bath on the unprotected portions of the porcelain is dependent on such factors as the concentration of the acid solution, the time of application of the acid-etching solution to the porcelain surface, and the temperature at which the bath is operated. Particularly good results have been obtained with solutions containing an acid concentration of approximately 12%.

In an alternative preferred embodiment of the invention, the aqueous acid-etching solution is contained in a sealed vessel which is immersed in an ultrasonic bath so as to agitate the solution during etching. It has been found that the use of ultrasonic agitation substantially increases the rate of acid attack on the porcelain, reducing the required time to about 10 minutes at room temperature where the acid concentration is approximately 12%.

In the practice of the present invention, a matrix for each individual tooth that is to be bonded to the acid-etched porcelain veneer facing is made on a model provided by the dentist or poured by the laboratory in an impression made by the dentist.

The basic component of the model consists of cast stone preferably treated with shellac, cyanoacralate solution or other equivalent material to prevent the porcelain veneer facing from becoming dehydrated and attached thereto. In the preferred practice, the matrix which covers the cast stone model is a very thin layer of dead soft platinum having a thickness in the range of from about 0.005 to about 0.015 inches. It is generally preferred to use a platinum sheet having a thickness on the order of 0.01 inches. Here too, however, it will be understood that any equivalent metal may also be used, such as palladium or gold, which will be apparent to persons of ordinary skill in the art.

Once the platinum matrix is prepared and put in place it functions as a base on which a porcelain veneer facing of the desired shape and form may be built. In preparing the porcelain veneer facing, a vacuum fired commercially available dental porcelain may be used, which conventionally are either of a low fusing grade (m.p. 1800° F.) or a high fusing grade (m.p. 2300° F.).

Upon completion of the build-up, the platinum matrix together with the porcelain veneer facing is carefully removed from the cast stone mold and is preheated at a temperature of about 1000° F. to about 1200° F. for a time of from about 10 minutes to about 12 minutes. The preheated build-up is then fired, preferably following the procedures recommended by the manufacturer of the particular porcelain material being used.

Once the firing cycle is completed the porcelain veneer facing is allowed to cool. Using conventional methods well known to persons of ordinary skill in the art, the porcelain veneer facing is shaped and brought to the desired final form and thereafter stained and glazed. The platinum matrix is then removed from the porcelain veneer facing and the feather edge of the porcelain is then preferably slightly buffed to remove any possible sharp edges.

The glazed portion of the porcelain veneer facing which is not desired to be acid-etched is then protected by some suitable masking material, preferably wax, which has a strong affinity for the porcelain and is impervious to the action of the hydrofluoric acid-etching bath. The thickness of the waxy protective layer preferably is on the order of about 1 mm. By this method, only those areas of the porcelain veneer facing which are to be affixed to the patient's tooth are acid-etched.

In general, the etching process of the present invention as preferably embodied comprises the step of contacting selected portions of the porcelain veneer facing to be acid-etched with a dilute solution of hydrofluoric acid at room temperature and for a period of time sufficient to produce the desired acid-etched surface. The preferred method of application in forming an acid-etched porcelain veneer facing is immersion. As previously mentioned, preferred conditions for producing the desired acid-etched surface include the use of a hydrofluoric acid solution having a concentration of about 12% for a time of between about 12 to 15 minutes. Of course, as will be apparent to persons of ordinary skill in the art, commercially satisfactory acid-etched surfaces may be obtained in shorter reaction times with etching solutions containing relatively higher acid concentration.

As also previously mentioned, in the preferred practice of the present invention, the acid-etching solution is contained in a sealed vessel which is immersed in a conventional ultrasonic bath so as to accelerate the etching process.

Advantageously, and as here preferably embodied, following completion of the etching step, the process of the present invention also includes the step of immersing the porcelain veneer facing in an ice water bath having a temperature of about 34° F.-38° F. for a period of time of between about one and two minutes so as to cause the waxy layer covering the glazed portion of the veneer facing to become brittle. Upon completion of the ice water immersion step the waxy layer can be easily removed from the porcelain veneer facing by scraping with a surgical blade or other suitable instrument.

At this point, the partially acid-etched porcelain veneer facing is ready for application to the patient's tooth. Prior to such application, the surface of the natural or virgin tooth to be covered is acid-etched by conventional procedures, in which the tooth is swabbed or brushed with a dilute solution of phosphoric acid, usually on the order of a 30-40% concentration. In most cases, no grinding or other tooth preparation procedure is required. Where some tooth preparation is required, only minimal tooth reduction should be necessary.

The surface of the porcelain veneer facing which has been acid-etched can be permanently and securely affixed directly to the patient's tooth with the use of a suitable dental bonding composition. Advantageously, the bonding composition may comprise either a light curable composition, such as "Ultra-Bond", available from the Den-Mat Corporation, Santa Maria, Calif. or a self-curable composition, such as "Concise", available from the 3M Company, Minneapolis, Minn. Each of these compositions has been found to provide highly satisfactory results, although the light curable compositions are believed more advantageous because they are somewhat easier for the dentist to handle. Other equivalent bonding compositions may also be used with equally satisfactory results, as will be apparent to persons of ordinary skill in the art.

It will be understood from the foregoing description that the process and product of the present invention has unusual and important commercial significance. It has not heretofore been known how to directly affix a porcelain veneer facing to the natural or virgin tooth. Using the surprisingly simple process of the present invention and commercially available materials, it has been unexpectedly found that a porcelain veneer facing can be selectively acid-etched and thereafter permanently and securely bonded directly to the natural tooth after acid-etching of the tooth by means of conventional procedures.

Since the process and advantages of the present invention may be readily understood from the foregoing description, further explanation is believed to be unnecessary. However, since numerous modifications will readily occur to those skilled in the art after a consideration of the foregoing specification, it is not intended that the invention be limited to the specific embodiments disclosed herein, but includes all suitable modifications and equivalents which fall within the scope of the appended claims.

Having described the invention, what is claimed is:

1. A method of etching a porcelain veneer facing for use in prosthetic dentistry to improve the adhesion thereof to a natural or virgin tooth of a dental patient, which method comprises:

forming a porcelain veneer facing of the desired shape and form;

covering the portions of said porcelain veneer facing which will be visible in the patient's mouth with a protective waxy material which has a strong affinity for porcelain and is impervious to acid;

contacting said porcelain veneer facing with an aqueous acidic solution for a period of time sufficient to effect a reaction between said solution and said porcelain veneer facing to produce an etching on the unprotected areas of said porcelain veneer facing; and removing said protective waxy material from said porcelain veneer facing.

2. The method as recited in claim 1 wherein the partially covered porcelain veneer facing is immersed in an aqueous solution of hydrofluoric acid.

3. The method as recited in claim 1, including the step of immersing the etched porcelain veneer facing in an ice water bath to facilitate removal of the waxy protective material.

4. A dental prosthesis comprising an acid-etched porcelain veneer facing produced by the method of claim 1.

5. A method as claimed in claim 1, including the steps of:

acid-etching the surface of the natural or virgin tooth which is to receive the etched porcelain veneer facing;

applying a bonding composition to at least one of said etched porcelain and said etched tooth surfaces; and adhering the etched surface of said porcelain veneer facing directly to the etched surface of said natural or virgin tooth by said bonding composition.

6. The method as claimed in claim 2, wherein the hydrofluoric acid concentration in said solution is preferably between about 10% to 15%.

7. A dental prosthesis comprising an acid-etched porcelain veneer facing produced by the method of claim 2.

8. The method as claimed in claim 5, wherein said bonding composition is light curable.

9. The method as claimed in claim 5, wherein said bonding composition is self-curable.

10. The method as claimed in claim 5, wherein the surface of said natural or virgin tooth is etched by contacting said tooth surface with a dilute solution of phosphoric acid.

11. The method as claimed in claim 5, wherein said hydrofluoric acid concentration is about 12%, said solution is at room temperature and said porcelain veneer facing is contacted with the hydrofluoric acid solution for a period of time of from about 12 to about 15 minutes.

12. The method as claimed in claim 5, wherein said hydrofluoric acid concentration is about 12%, said porcelain veneer facing and said hydrofluoric acid solution are contained in a sealed vessel at room temperature and said vessel is immersed in an ultrasonic agitation bath for a period of about 10 minutes.

* * * * *